United States Patent [19]
Karrenbauer et al.

[11] Patent Number: 4,550,200
[45] Date of Patent: Oct. 29, 1985

[54] PROCESS FOR OBTAINING D,L-HOMOCYSTINE (II)

[75] Inventors: Michael Karrenbauer, Rodenbach; Axel Kleemann, Hanau; Theodor Lüssling, Konstanz-Litzelstetten; Fritz Schäfer, Konstanz, all of Fed. Rep. of Germany

[73] Assignee: Degussa Aktiengesellschaft, Frankfurt, Fed. Rep. of Germany

[21] Appl. No.: 590,059

[22] Filed: Mar. 15, 1984

[30] Foreign Application Priority Data

Mar. 18, 1983 [DE] Fed. Rep. of Germany ....... 3309762

[51] Int. Cl.$^4$ ......................................... C07C 149/243
[52] U.S. Cl. ................................................... 562/556
[58] Field of Search .................. 562/556, 557; 568/26

[56] References Cited
U.S. PATENT DOCUMENTS 3,565,959  2/1971  Takase .................................. 568/26
3,978,137  8/1976  Frame .................................. 568/26

FOREIGN PATENT DOCUMENTS 621915  9/1949  United Kingdom .

OTHER PUBLICATIONS

Abderhalden, Chem. Abst., 17; 1810–1811 (1923).
Harris, Biochem. J., 16, pp. 739–746 (1922).
Reid, "Organic Chemistry of Bivalent Sulfur," vol. I, pp. 118–124 & 460–467 (1958).

Primary Examiner—Michael L. Shippen
Attorney, Agent, or Firm—Cushman, Darby & Cushman

[57] ABSTRACT

D,L-Homocystine is obtained by introducing molecular oxygen into an aqueous solution of the disodium salt of D,L-homocysteine having a concentration between 0.8 and 1.2 moles/l and an initial pH between 7.0 and 8.0 in the presence of a catalytic amount of iron(III) ions until there is no longer an increase in pH and subsequently adjusting the pH to about 5.3 with stirring.

7 Claims, No Drawings

PROCESS FOR OBTAINING D,L-HOMOCYSTINE (II)

BACKGROUND OF THE INVENTION

The present invention is directed to a process for obtaining D,L-homocystine by oxidation of the disodium salt of D,L-homocysteine.

D,L-homocystine is of interest in the production of food for domestic animals.

Of course it is known to oxidize mercaptans to the corresponding disulfides. In the case of D,L-homocysteine, however, there are obtained high yields of the desired D,L-homocystine only by maintaining specific conditions.

SUMMARY OF THE INVENTION

The process of the invention comprises obtaining D,L-homocystine by introducing molecular oxygen into an aqueous solution of the disodium salt of D,L-homocysteine having a concentration between 0.8 and 1.2 moles/l and an initial pH between 7.0 and 8.0 in the presence of a catalytic amount of iron (III) ions until there is no longer an increase in pH and subsequently adjusting the pH to about 5.3 with stirring.

Surprisingly under the reaction conditions the desired D,L-homocystine is obtained in yields of over 80%. In contrast if there is treated the aqueous solution of the disodium salt of D,L-homocysteine having a concentration of less than 0.8 mole/l or more than 1.2 moles/l or with an initial pH of less than 7.0 or more than 8.0, there are obtained clearly lower yields.

The aqueous solutions of the disodium salt of D,L-homocysteine serving as starting materials can be produced in known manner by demethylation of D,L-methionine by means of sodium in liquid ammonia, subsequent vaporization of the ammonia and taking up the residue remaining in a suitable amount of water.

The adjustment of the initial pH to a value between 7.0 and 8.0 is carried out suitably with an aqueous mineral acid, preferably hydrochloric acid. However, other mineral acids can be used, e.g. sulfuric acid, hydrobromic acid, phosphoric acid.

The oxidation is carried out in the presence of a catalytic amount, for example 50 to 500 mg per mole of disodium salt of D,L-homocysteine employed, of iron (III) ions.

The end of the oxidation reaction is recognized when no increase in pH occurs upon further introduction of molecular oxygen. This is generally the case after about 3 to 5 hours.

After the end of the oxidation the pH of reaction mixture is adjusted to about 5.3, suitably with an aqueous mineral acid, preferably hydrochloric acid. It is advantageous if the adjustment of the pH is carried out a elevated temperature, for example, 50° C. and subsequently the reaction mixture is cooled to room temperature slowly with stirring, for example in the course of one hour. The D,L-homocystine is obtained in a particularly advantageous crystalline form if the stirring speed is regulated during the precipitation in such manner that the D,L-homocystine is obtained directly in suspension. Then it can be separated off especially easily by filtration or centrifugation.

Unless otherwise indicated all parts and percentages are by weight.

The process can comprise, consist essentially of, or consist of the stated steps with the recited materials.

The invention will be explained in more detail through the following examples and comparison experiments.

DETAILED DESCRIPTION

Example 1

13.95 grams of the disodium salt of D,L-homocysteine produced by demethylation of D,L-methionine were dissolved in water and treated with hydrochloric acid so that there was formed a 0.8 molar solution having a pH of 7.0. This solution was then treated with 77 mg of iron (III) sulfate. Subsequently there were led in within 3 hours at 25° C. 99.6 dm$^3$ of oxygen (the large excess of oxygen can be explained by the considerable losses in passing through which are not considered). The reaction mixture was then heated to 50° C. and adjusted to a pH of 5.3 with 10% hydrochloric acid with stirring. The mixture was cooled to room temperature within one hour with stirring. The precipitated D,L-homocystine was filtered off with suction, washed with 100 ml of water at 80° C. and dried in a vacuum drier to constant weight. The yield of D,L-homocystine was 9.2 grams, corresponding to 88% of theory.

Example 2

Example 1 was repeated with the difference that the disodium salt of D,L-homocysteine was treated with sufficient water and hydrochloric acid that there was formed a 0.8 molar solution having a pH of 8.0. The yield of D,L-homocystine was 9.6 grams, corresponding to 92% of theory.

Comparison Experiment 1

Example 1 was repeated with the difference that the disodium salt of homocysteine was treated with sufficient water and hydrochloric acid that there was formed a 0.8 molar solution having a pH of 9.0. The yield of D,L-homocystine was 3.2 grams, corresponding to 30.6% of theory.

Example 3

20.85 grams of the disodium salt of D,L-homocysteine produced by demethylation of D,L-methionine were dissolved in water and treated with hydrochloric acid so that there was formed a 1,2 molar solution having a pH of 8.0. Subsequently there was introduced oxygen in a manner analogous to example 1 and the reaction mixture was worked up. The yield of D,L-homocystine was 14.83 grams, corresponding to 95% of theory.

Comparison Experiment 2

Example 3 was repeated with the difference that the disodium salt of D,L-homocysteine was treated with sufficient water and hydrochloric acid that there was formed a 1.4 molar solution having a pH of 8.0. The yield of D,L-homocystine was 7.49 grams, corresponding to 48% of theory.

Comparison Experiment 3

Example 3 was repeated with the difference that the disodium salt of homocysteine was treated with sufficient water and hydrochloric acid that there was formed a 0.4 molar solution having a pH of 8.0. The yield of D,L-homocystine was 8.96 grams, corresponding to 57.4% of theory.

What is claimed is:

1. A process for obtaining D,L-homocystine comprising introducing molecular oxygen into an aqueous solution of the disodium salt of D,L-homocysteine having a concentration between 0.8 and 1.2 moles/l and an initial pH between 7.0 and 8.0 in the presence of a catalytic amount of $Fe^{3+}$ ions until there is no longer an increase in pH and subsequently adjusting the pH to about 5.3 with stirring.

2. A process according to claim 1 wherein the oxidation is carried out in the presence of iron (III) sulfate.

3. A process according to claim 2 wherein there are employed 50 to 500 mg of the $Fe^{3+}$ ions per mole of the disodium salt of D,L-homocysteine.

4. A process according to claim 1 wherein there are employed 50 to 500 mg of the $Fe^{3+}$ ions per mole of the disodium salt of D,L-homocysteine.

5. A process according to claim 1 wherein the sole materials employed are the disodium salt of D,L-homocysteine, water, molecular oxygen $Fe^{3+}$ ions and the ions of a mineral acid.

6. A process according to claim 5 wherein the mineral acid ions are selected from the group consisting of ions of hydrochloric acid, sulfuric acid, hydrobromic acid, phosphoric acid or mixtures thereof.

7. A process according to claim 6 wherein there are employed Fe (III) sulfate and hydrochloric acid.

* * * * *